United States Patent

Wytcherley et al.

[11] Patent Number: 5,492,625
[45] Date of Patent: Feb. 20, 1996

[54] METHOD OF RECOVERING CARBOXYLIC ACIDS FROM DILUTE SOLUTIONS

[75] Inventors: Randa W. Wytcherley, Belgrade, Mont.; Joseph C. Gentry, Houston; Ronald G. Gualy, Dallas, both of Tex.

[73] Assignee: Glitsch, Inc., Dallas, Tex.

[21] Appl. No.: 224,601

[22] Filed: Apr. 7, 1994

[51] Int. Cl.$^6$ .......................... B01D 61/00; B01D 11/00
[52] U.S. Cl. ......................... 210/634; 210/651; 210/650; 210/652; 210/653; 210/654; 210/655; 210/641; 203/10; 203/15; 203/16; 203/14; 203/43; 203/48
[58] Field of Search ..................... 210/644, 634, 210/650–654, 641, 500.3, 500.38, 500.41, 500.42, 500.21, 490, 655; 203/10, 15, 16, 14, 48, 43

[56] References Cited

U.S. PATENT DOCUMENTS

| | | |
|---|---|---|
| 2,953,502 | 9/1960 | Binning et al. . |
| 3,182,043 | 5/1965 | Kirkland . |
| 3,808,267 | 4/1975 | Davis et al. . |
| 4,576,683 | 3/1986 | Cohen ................................. 203/15 |
| 4,661,208 | 4/1987 | Honma et al. ...................... 203/15 |
| 4,729,818 | 3/1988 | Berg ................................... 203/16 |
| 4,808,287 | 2/1989 | Hark ................................... 210/641 |
| 4,838,998 | 6/1989 | Davies et al. ....................... 203/15 |
| 4,909,939 | 3/1990 | Rickelton et al. .................. 210/634 |
| 5,104,492 | 4/1992 | King et al. .......................... 203/15 |
| 5,250,182 | 10/1993 | Bento et al. ........................ 210/641 |

FOREIGN PATENT DOCUMENTS

| | | |
|---|---|---|
| 0091799 | 6/1982 | Japan . |
| 118538 | 7/1983 | Japan . |
| 9323150 | 11/1993 | WIPO . |

OTHER PUBLICATIONS

EPO Search Report for Application EP 94 306892, Feb. 2, 1995.

Primary Examiner—Robert A. Dawson
Assistant Examiner—Ana M. Fortuna
Attorney, Agent, or Firm—Jenkens & Gilchrist

[57] ABSTRACT

A method for recovering carboxylic acids from a dilute aqueous solution thereof having a concentration below about ten percent (10%) by weight, which includes passing the dilute acid solution through a reverse osmosis separator, thereby producing a permeate substantially free of acid and a retentate having an acid concentration above about ten percent (10%) by weight. The retentate is contacted with a liquid extractant for acids to produce an acid-rich extractate and an acid-free raffinate. The acid is then recovered from the acid-rich extractate.

11 Claims, 1 Drawing Sheet

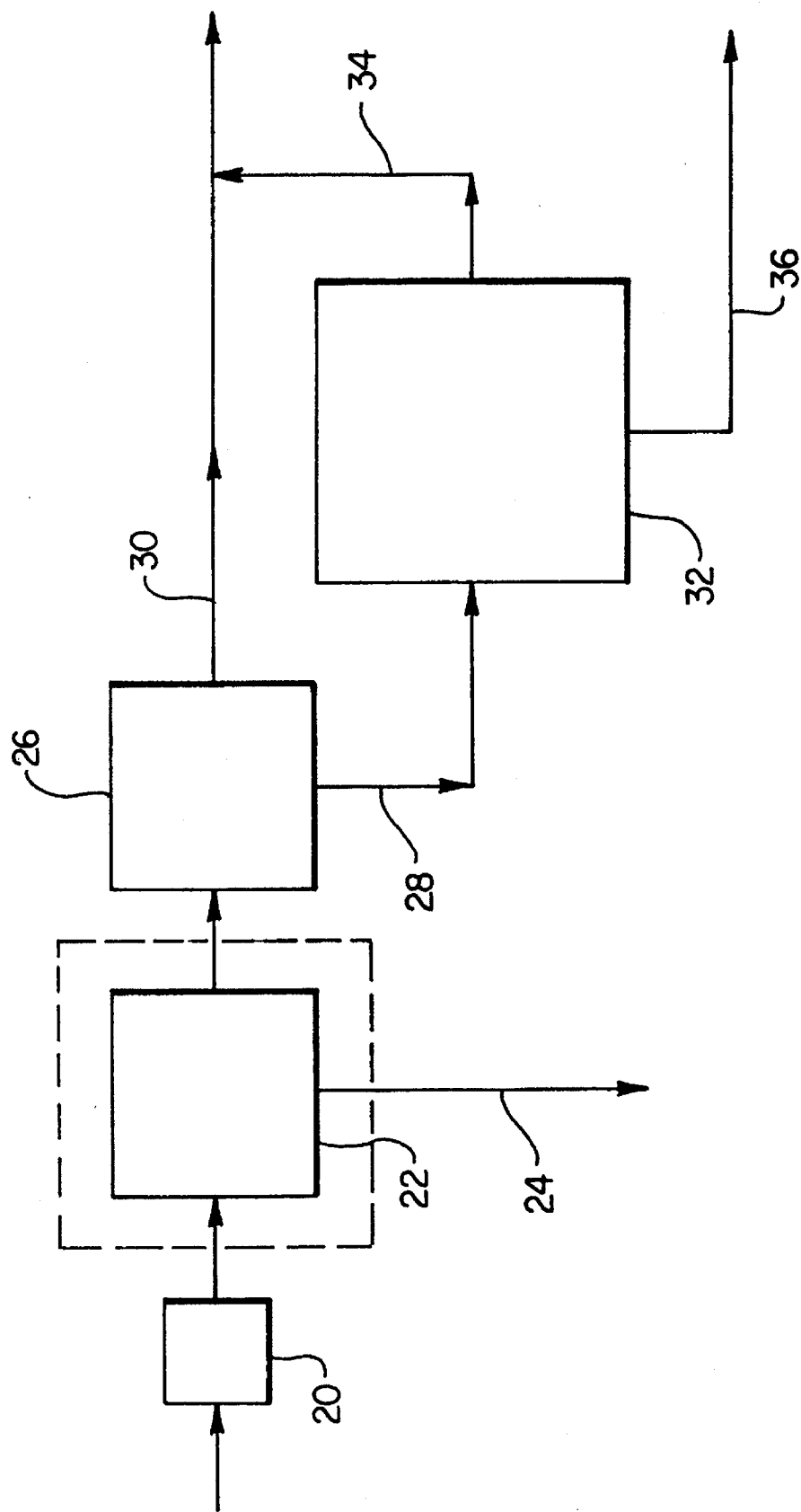

METHOD OF RECOVERING CARBOXYLIC ACIDS FROM DILUTE SOLUTIONS

This invention relates to methods and apparatus for recovering carboxylic acids from dilute solutions thereof by the use of reverse osmosis membrane systems in combination with other acid recovery techniques.

BACKGROUND OF THE INVENTION

Many industrially important processes result in the production of streams of carboxylic acids in dilute concentrations. Economic considerations and environmental concerns lead to the desirability of recovering carboxylic acids from such streams for reuse, for sale, or for disposal in the most economic manner.

Experience has shown that carboxylic acids in dilute concentrations, i.e. below about fifteen percent (15%) by weight, in aqueous streams, are most economically removed and recovered through the use of a liquid-liquid extraction process employing a high-boiling solvent. When the carboxylic acids make up less than about three percent (3%) by weight of the stream to be treated, it becomes difficult to recover the acids economically by such a liquid-liquid extraction process, although environmental considerations often make it necessary to treat such streams nonetheless. In accordance with the present invention, methods and apparatus are provided for pre-concentrating dilute carboxylic acid streams having a low concentration of acids, following which the relatively more concentrated streams so produced are further treated, as by liquid-liquid extraction to recover the carboxylic acids they contain with better economic performance.

SUMMARY OF THE INVENTION

In accordance with the invention, it has been discovered that subjecting a dilute carboxylic acid aqueous stream having a concentration of less than ten percent (10%) by weight acid to an initial treatment step of a membrane separation, preferably reverse osmosis separation in a reverse osmosis membrane system, to produce a more concentrated carboxylic acid intermediate stream having an acid concentration which is materially above the starting concentration, and in most cases above about ten percent (10%) by weight, and then subjecting that intermediate stream to a further separation process, preferably liquid-liquid extraction, to produce an extractate, which in turn can be subjected to further acid separation steps, preferably distillation, to recover a purified and concentrated carboxylic acid product stream, is an efficient and effective recovery method. It is preferred that the extractant employed in the liquid-liquid extraction step be a high-boiling material, for example secondary and tertiary amines such as those under the trademarks Adogen™ by Sherex, Amberlite™ by Rohm & Haas, Hosterex™ by Hoechst, or alkyl phosphine oxides sold under the trademark Cyanex™ by Cytec Industries. Other separation processes besides liquid-liquid extraction which may be used following the membrane separation process include extractive distillation, azeotropic distillation and classical distillation.

More particularly, the present invention contemplates a method and apparatus for recovering carboxylic acids from a dilute aqueous solution thereof which has an acid concentration below about ten percent (10%) by weight. The method includes passing the dilute acid solution through a membrane separator to thereby produce an aqueous permeate substantially free of acid and an aqueous retentate having an acid concentration above about ten percent (10%) by weight. The retentate is then contacted with a liquid extractant for acids to produce an acid-rich extractate and a substantially acid-free raffinate. The carboxylic acid is then recovered from the acid-rich extractant. The method of the invention is particularly effective when the carboxylic acids are from the class consisting of formic, acetic, propionic, and butyric acids and mixtures thereof. More generally speaking, the invention is useful for recovering carboxylic acids having from one (1) to seven (7) carbon atoms and preferably two (2) to four (4) carbon atoms. In a preferred form of the invention, the carboxylic acid is recovered from the acid-rich extractate by a distillation step.

In a further preferred form of the invention, the dilute aqueous solution of carboxylic acids is subjected to a preliminary treatment step prior to being subjected to reverse osmosis separation in order to remove impurities such as aromatic carboxylic acids, metallic ions, free metal particles, organic or inorganic salts, straight chain carboxylic acids having more than five (5) carbon atoms, and sugars, along with other similar impurities. The impurity removal step may be performed by filtration, microfiltration, ultrafiltration, nanofiltration, or a combination of two or more of such processes. In further accordance with the invention, the membrane separator employed therein may utilize a semi-permeable membrane formed from a material such as polysulfone, polyether sulfone, cellulose acetate, polyamide, cellulose esters, cellulose triacetate, polyether urea, polyvinyl alcohol, polypiperiazamide, polyfuren, cellulose acetate butyrate, aromatic polyamide, polyethyleneimine, and thin film composites of any of the above.

BRIEF DESCRIPTION OF THE FIGURE

The single FIGURE of the drawing illustrates in block diagram form a flow diagram for a preferred process of the invention.

DETAILED DESCRIPTION OF A PREFERRED EMBODIMENT

In the FIGURE, the process streams flow generally from left to right through the system. The equipment for practicing the invention includes a pre-treatment section 20, which may be a single or multiple stage filtration, microfiltration, ultrafiltration, or nanofiltration device, or a combination of such devices. If the stream to be treated is sufficiently clean, the pre-treatment step or stage 20 may be omitted.

Preferably, another pre-treatment stage 22, which is preferably a nanofiltration stage, is employed in the process of the invention. One of the output streams from the nanofiltration step, the filter concentrate, comprises a concentrated stream of heavy impurities, which are withdrawn from the system in known manner and directed to recovery equipment or are otherwise disposed of. Such withdrawal is shown as occurring through line 24.

The next stage in the preferred operation of the invention is a membrane separator stage 26. The equipment includes a semi-permeable membrane having the property of rejecting carboxylic acids in large part and passing water. The output streams from the reverse osmosis stage 26 include a retentate stream 28 and a permeate stream 30.

The permeate stream 30 is substantially pure water and is passed to disposal or reuse within the plant in which the process is being practiced. If desired, the permeate may be passed through additional reverse osmosis stages similar to stage 26 or forming a part thereof to enhance the recovery of carboxylic acids which may be residually present in the permeate stream. Similarly, the retentate passing through retentate stream 28 may be subjected to additional reverse osmosis treatment to produce a higher concentration of carboxylic acids in the retentate stream, and to produce subsidiary permeate streams which may be combined with permeate stream 30, or disposed of separately or returned separately for use within the plant in which the process of the invention is being practiced.

The retentate passing through line 28 is then subjected to a liquid-liquid extraction treatment in extraction-recovery-purification stage 32, and the raffinate resulting from such treatment leaves the system through line 34. The raffinate is substantially pure water and may disposed of or reused in the plant in which the invention is being practiced. The acid-rich extractant may be separated by distillation or by other recovery and purification methods which may involve, if desired, multiple stages. Such treatments eventually produce purified acids which leave the system of the invention through line 36.

What is claimed is:

1. A method for recovering carboxylic acids from a dilute aqueous acid solution, said dilute acid solution having an acid concentration below about ten percent (10%) by weight, and containing one or more impurities from the class consisting of aromatic carboxylic acids, metallic ions, free metal particles, organic or inorganic salts, straight chain carboxylic acids having more than five (5) carbon atoms and sugars, comprising:

removing said impurities from said dilute aqueous solution;

passing said dilute acid solution through a membrane separator having a semi-permeable membrane, to thereby produce an aqueous permeate substantially free of acid and an aqueous retentate having an acid concentration more concentrated than the initial concentration of said dilute acid solution;

treating said retentate in an acid separation step to thereby produce a further concentrate acid solution and a substantially acid-free raffinate; and recovering acid from said further concentrate acid solution.

2. A method in accordance with claim 1 in which said membrane separator is a reverse osmosis membrane separator.

3. A method in accordance with claim 2 in which said reverse osmosis separator employs a semi-permeable membrane formed from a material selected from the class consisting of polysulfone, polyether sulfone, cellulose acetate, polyamide, cellulose esters, cellulose triacetate, polyether urea, polyvinyl alcohol, polypiperiazamide, polyfuren, cellulose acetate butyrate, aromatic polyamide, polyethyleneimine, and thin film composites of any of the above.

4. A method in accordance with claim 1 in which said aqueous retentate has an acid concentration above about ten percent (10%) by weight.

5. A method in accordance with claim 1 in which said acid separation step comprises contacting said retentate with a liquid extractant for acids to thereby produce an acid-rich extractate and a substantially acid-free raffinate, and recovering acid from said acid-rich extractate.

6. A method in accordance with claim 5 in which acid is recovered from said acid-rich extractate by distillation.

7. A method in accordance with claim 1 in which said acid separation step comprises extractive distillation.

8. A method in accordance with claim 1 in which said acid separation step comprises distillation.

9. A method in accordance with claim 1 in which said carboxylic acids are from the class consisting of acids having from one (1) to seven (7) carbon atoms and mixtures thereof.

10. A method in accordance with claim 9 in which said acids are from the class of acids consisting of acids having from two (2) to four (4) carbon atoms and mixtures thereof.

11. A method in accordance with claim 1 in which said impurities are removed from said dilute aqueous carboxylic acid solution by filtration, microfiltration, ultrafiltration, nanofiltration, or a combination of two or more of said processes.

* * * * *